US005354274A

United States Patent [19]

Demeter et al.

[11] Patent Number: 5,354,274

[45] Date of Patent: Oct. 11, 1994

[54] DEVICE FOR ORAL ADMINISTRATION OF LIQUIDS

[75] Inventors: Robert J. Demeter, Mooresville; Stephen F. Badylak, West Lafayette; Kirk S. Foster, West Lafayette; Leslie A. Geddes, West Lafayette, all of Ind.

[73] Assignees: Methodist Hospital of Indiana, Inc., Indianapolis; Purdue Research Foundation, West Lafayette, both of Ind.

[21] Appl. No.: 932,790

[22] Filed: Aug. 20, 1992

[51] Int. Cl.$^5$ ........................ A61M 31/00; A61J 17/00

[52] U.S. Cl. ........................ 604/77; 215/11.1; 606/234

[58] Field of Search ................. 604/77, 200, 201, 206; 215/11.1, 11.3, 11.4; 606/234–236

[56] References Cited

U.S. PATENT DOCUMENTS

| | | | |
|---|---|---|---|
| D. 196,090 | 8/1963 | Barton et al. . | |
| 1,656,833 | 1/1928 | Schutze . | |
| 2,612,165 | 9/1952 | Szuderski . | |
| 2,780,378 | 2/1957 | Romano | 215/11 |
| 2,807,384 | 9/1957 | Lipari | 215/11.1 |
| 2,824,561 | 2/1958 | Mueller . | |
| 2,876,113 | 3/1959 | Barton | 99/171 |
| 2,889,829 | 6/1959 | Tannenbaum et al. . | |
| 3,143,429 | 8/1964 | Swanson et al. | 99/171 |
| 3,146,904 | 9/1964 | Hansen et al. | 215/11.1 |
| 3,255,923 | 6/1966 | Soto | 215/11.3 |
| 3,294,268 | 12/1966 | Barton et al. | 215/11 |
| 3,426,755 | 2/1969 | Clegg . | |
| 3,610,248 | 10/1971 | Davidson . | |
| 3,662,756 | 5/1972 | Hakim . | |
| 3,784,039 | 1/1974 | Marco . | |
| 4,078,566 | 3/1978 | Urban, Jr. . | |
| 4,237,884 | 12/1980 | Erickson et al. . | |
| 4,412,623 | 11/1983 | Schmidt | 215/11.1 |
| 4,540,405 | 9/1985 | Miller et al. | 604/232 |
| 4,637,934 | 1/1987 | White | 215/11.1 |
| 4,640,424 | 2/1987 | White | 215/11.1 |
| 4,657,151 | 4/1987 | Cabernoch | 215/11.1 |
| 4,706,827 | 11/1987 | Cabernoch et al. | 215/11.1 |
| 4,722,850 | 2/1988 | White et al. | 215/11.1 |
| 4,768,510 | 9/1988 | Leung . | |
| 4,867,159 | 9/1989 | Fulton . | |
| 4,898,291 | 2/1990 | Sailors | 215/11.4 |
| 4,959,051 | 9/1990 | Glass et al. | 604/77 |
| 5,013,321 | 5/1991 | MacVane | 606/234 |
| 5,123,915 | 6/1992 | Miller et al. | 604/77 |
| 5,127,903 | 7/1992 | Mailot et al. | 604/77 |

FOREIGN PATENT DOCUMENTS

| | | | |
|---|---|---|---|
| 874 | of 1908 | United Kingdom . | |
| 210888 | 2/1924 | United Kingdom . | |
| 754476 | 8/1956 | United Kingdom | 604/77 |
| 788905 | 1/1958 | United Kingdom . | |

*Primary Examiner*—Ralph Lewis
*Attorney, Agent, or Firm*—Barnes & Thornburg

[57] ABSTRACT

A device is provided for facilitating oral administration of unit dosages of liquid formulations, particularly to pediatric and geriatric patients. Sealed cartridges containing unit doses of liquid nutrients or medications can be locked into the device and at the same time, breached so that the contained-liquid formulation can flow from the cartridge into a hollow nipple for facile oral consumption. The liquid formulation-contained sealed cartridge includes a container having a side wall collapsible responsive to withdrawal of liquid from the hollow nipple.

20 Claims, 4 Drawing Sheets

DEVICE FOR ORAL ADMINISTRATION OF LIQUIDS

BACKGROUND AND SUMMARY OF THE INVENTION

This invention relates to a device for oral administration of liquid formulations. More particularly, the invention is directed to a pacifier-like device for dispensing a unit dose of a liquid nutrient or medication from a sealed cartridge into a hollow nipple for facile consumption by pediatric and geriatric patients.

Many medicines and nutrients are formulated as liquids for oral administration. Parents, nurses, and physicians are often challenged by the task of administering such liquids to newborns, infants, toddlers and even the elderly. The present invention was developed responsive to what has been perceived as the very significant need to facilitate oral drug delivery to these special patients.

It is known to use a modified pacifier to deliver a liquid to an infant. For example, U.S. Pat. No. 5,013,321 discloses a pacifier for delivery of a flavored gel to an infant through a nipple; U.S. Pat. Nos. 2,889,829 and 4,867,159 disclose pacifiers that can be filled with syrups and liquified medicines, respectively; and U.S. Pat. Nos. 2,824,561 and 3,426,755 disclose medicine feeders. Also, a dual-chambered container for delivery of a liquid medicament through a nipple is disclosed in U.S. Pat. No. 4,959,051, and a pacifier accommodating a porous medication container is disclosed in U.S. Pat. No. 2,612,165.

Although liquid-dispensing pacifiers are known, many pacifiers are not well-suited for delivering unit doses of medicines or other liquid formulations. Measuring and administering the small volume (dose) of a liquid formulation presents a problem that often makes it difficult or inconvenient to use a pacifier-like delivery device for oral administration of medicines. A device configured to utilize a sealed cartridge containing a pre-measured volume of liquid medicine, nutrients, or the like would provide a significant improvement over known liquid-dispensing pacifiers. Not only would it simplify the task of dispensing orally administrable liquid formulations, but it would, as well, provide more accurate control of dosage levels.

According to the present invention, a pacifier-like device is provided for dispensing liquid formulations orally to patients who might resist efforts to administer oral dosage forms by typical oral dosing techniques. The device includes a hollow nipple, a hollow handle formed to include a cartridge-receiving cavity, a base trapped between the nipple and the handle and arranged to cover the mouth of the cavity, and a means for positioning liquid formulation-containing sealed cartridge inside the cavity of the hollow handle in liquid sealed contact with a port in the base, further cooperating with means for positioning and retaining (or locking) the cartridge in the device.

The device further includes means for conducting the liquid formulation from the sealed cartridge through the base into the hollow nipple to allow consumption of the liquid by a patient sucking on the nipple and means for puncturing or otherwise breaching the liquid formulation-containing sealed cartridge as it is positioned in contact with the base. The puncturing means can include the liquid conducting means, for example, a liquid transfer conduit extending through a port formed in the base.

Illustratively, either pre-filled sealed cartridges or cartridges filled by a parent and sealed prior to use are conveniently used in the improved pacifier. Such a pre-filled or refillable liquid formulation-containing sealed cartridge is positioned and retained in a fluid-sealed relationship with the liquid conducting means and the base. Advantageously, the cartridge-puncturing means cooperates with the cartridge-locking means to puncture the sealed cartridge as it is locked in place to the base.

In preferred embodiments, the liquid transfer conduit is a tubular member having one obliquely cut (pointed) open end for puncturing the sealed cartridge to communicate with liquid formulation contained in the cartridge and an opposite open end for discharging liquid formulation transferred from the punctured cartridge into the hollow nipple. The sealed cartridge includes a container having an orifice and a closure member for the container in fluid-sealing contact with the container orifice. The pointed open end of the liquid transfer conduit is arranged to puncture the closure member and extend into the container as the sealed cartridge is positioned in the pacifier device.

The puncturing means further includes means for mechanically locking the sealed cartridge to the base to hold the cartridge in a fixed position inside the cavity formed in the hollow handle. Illustratively, the locking means includes a cartridge holder having a housing for receiving the sealed cartridge and a turn-to-lock locking flange appended to the housing. The base is formed to include a slot for receiving the turn-to-lock locking flange. As the cartridge holder is locked into the base, the pointed end of the liquid transfer conduit punctures the closure of the sealed cartridge to establish fluid communication between the liquid-containing cartridge and the hollow nipple.

Advantageously, it is most convenient to load the present pacifier device with a pre-filled liquid formulation-containing cartridge for delivery to a patient. Further, it is a simple task to replace an empty cartridge with a new cartridge each time a liquid formulation dose is to be administered. It will be understood that the improved delivery device of the present invention may be adapted for in veterinary science applications for dispensing liquid formulations to animals.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
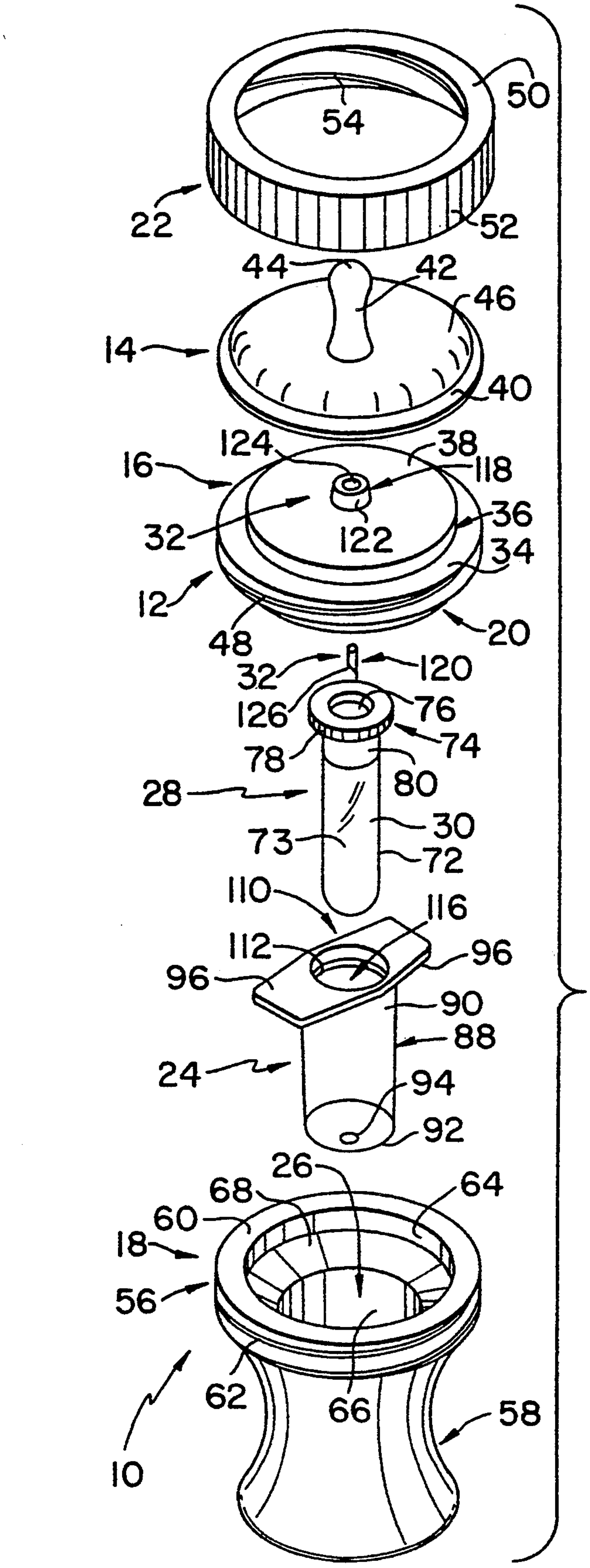
FIG. 1 is an exploded perspective view of a preferred embodiment of the present invention showing the locking ring, nipple, base, sealed cartridge, cartridge holder, and hollow handle.

A device for oral administration of liquid formulations from sealed cartridges through a perforate hollow nipple is illustrated in FIG. 1. Advantageously, the sealed cartridge is breached as it is being locked in place in the device so that the contained liquid formulation is accessible, for example, to an infant sucking on the nipple of the pacifier.

Referring to FIG. 1, an improved pacifier 10 includes a base 12, a nipple 14 for mounting on an outer side 16 of the base 12, a hollow handle 18 for mounting on an inner side 20 of the base 12, and a locking ring 22 for locking the nipple 14 and the hollow handle 18 to the base 12. A cartridge holder 24 is sized to fit in an open cavity 26 provided in hollow handle 18. The cartridge holder 24 is configured to be attachable to and detachable from the inner side 20 of the base 12.

A liquid formulation-containing sealed cartridge 28 is provided to supply liquid formulation 30 to the nipple 14 for consumption by a patient using the pacifier 10. The sealed cartridge 28 is sized to be positioned inside the cartridge holder 24. A liquid transfer conduit 32 extends through the base 12 to provide a means for puncturing or otherwise breaching the sealed cartridge 28 and conducting liquid formulation 30 from the sealed cartridge 28 through the base 12 into the hollow nipple 14.

The outer side 16 of base 12 includes an annular top seat 34 for supporting nipple 14 and a round disc 36 having a top surface 38. The nipple 14 includes an annular flange 40 for engaging the annular top seat 34 on base 12, a mouthpiece 42 formed to include one or more outlet apertures 44, and a flexible diaphragm 46 connecting the mouthpiece 42 to the annular flange 40 and overlying the top surface 38 of round disc 36. Base 12 also includes a perimeter edge 48 that is formed to include external threads to permit easy attachment to the locking ring 22. Locking ring 22 includes an annular top rim 50 and an annular side wall 52 formed to include internal threads 54 for coupling to the base 12 and the hollow handle 18.

Figure 3:
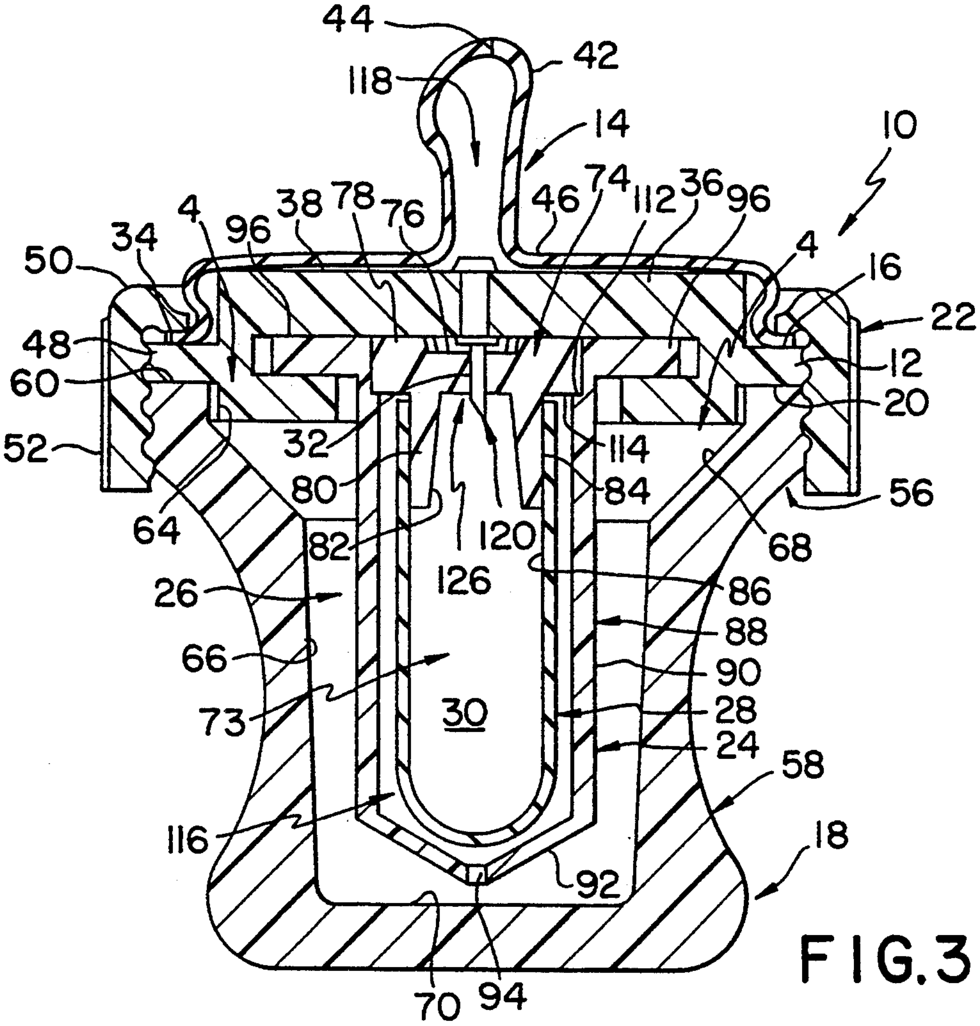
FIG. 3 is a sectional view of the fully assembled pacifier of FIG. 1 showing the engagement of the turn-to-lock locking flanges and the base to anchor the cartridge holder to the base and support the sealed cartridge so that the sealed cartridge is punctured by the liquid transfer conduit as the cartridge holder is being anchored to the base.

Hollow handle 18 includes a mounting portion 56 and a grip portion 58 as shown, for example, in FIGS. 1 and 3. It will be understood that it is within the scope of the invention to configure the grip portion 58 in many different ways to provide means for allowing device users to hold the pacifier 10 during assembly and use. In fact, an empty baby bottle could be used to provide a suitable hollow handle in accordance with the present invention.

Mounting portion 56 of hollow handle 18 illustratively includes an annular top seat 60 for supporting the annular flange 40 of nipple 14 and a perimeter edge 62 that is formed to include external threads to permit easy attachment of handle 18 to the locking ring 22. The hollow handle 18 further includes an interior upper annular side wall 64, an interior lower annular side wall 66, an axially inwardly converging conical wall 68 interconnecting side walls 64 and 66, and a bottom wall 70. These walls 64, 66, 68, and 70 cooperate to define the open cavity 26 in the hollow handle 18 and open cavity 26 is sized to be large enough to hold the cartridge holder 24 therein as shown best in FIG. 3.

Sealed cartridge 28 includes a container 72 formed to include a liquid-formulation reservoir 73 therein and a closure member 74 for covering the orifice of container 72 to seal liquid formulation 30 in the reservoir 73. As shown best in FIG. 3, closure member 74 includes a central thin membrane 76 that is easily punctured by the sharpened end of the liquid transfer conduit 32 as the sealed cartridge 28 is loaded into the pacifier 10. Closure member 74 also includes an annular rim 78 around the thin membrane 76 and a cylindrical stopper member 80 depending from rim 78 and membrane 76. The stopper member 80 includes a tapered inner wall 82 and an outer wall 84 that is sized to fit through the open mouth of container 72 and sealingly engage an inner wall 86 around the open mouth of container 72.

Figure 4:
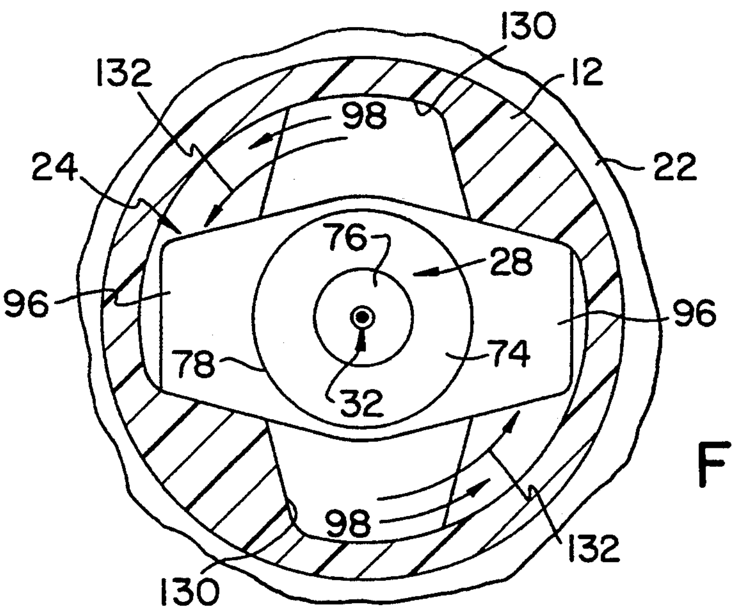
FIG. 4 is a sectional view taken along lines 4—4 of FIG. 3 showing the turn-to-lock locking flanges in place in the lock slots formed in the base following rotation of the cartridge holder about its longitudinal axis.
Figure 5:
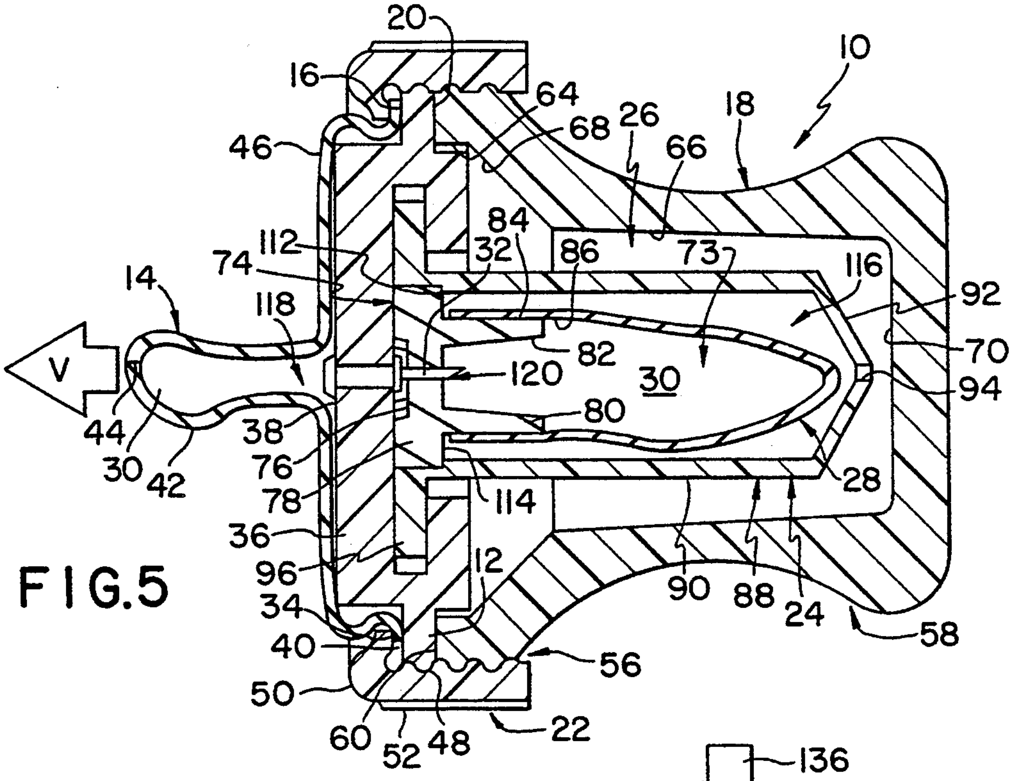
FIG. 5 is a view similar to FIG. 3 showing collapse of the cartridge as it would appear when an infant sucks on the nipple to draw liquid formulation out of the cartridge and into the nipple.

It will be understood that it is within the scope of the invention to provide either pre-filled sealed cartridges wherein the puncturable closure member is integral with the container or preassembled with the container at a factory or refillable sealed cartridges wherein the puncturable closure member is removable from, reattachable to, and resealable to the container in connection with the operation of the refilling of cartridge 28 with a liquid formulation. Illustratively, the container 72 is made of a flexible collapsible material such as latex rubber or polyethylene so that it will collapse as shown in FIG. 4 as an infant sucks on the mouthpiece 42 to draw liquid formulation from the sealed cartridge 28 into the hollow nipple 14 through the liquid transfer conduit 32. Further, the closure member 74 is preferably made of a puncturable material such as natural or synthetic rubber which is able to sealingly close the open mouth of container 72, yet is puncturable to permit the membrane 76 to be breached easily to permit insertion of the liquid transfer conduit 32 into the liquid-formulation reservoir 73 in the container 72.

Cartridge holder 24 is configured to support the sealed cartridge 28 as it is being punctured by the sharpened end of liquid transfer conduit 32. Cartridge holder 24 also anchors the sealed cartridge 28 to the underside 20 of base 12 during expulsion of liquid formulation 30 from sealed cartridge 28 into hollow nipple 14 through the liquid transfer conduit 32. Cartridge holder 24 includes a cylindrical housing 88 that is large enough to surround the container 72. Housing 88 includes a cylindrical side wall 90 and a bottom wall 92 that is formed to include a vacuum-relief aperture 94.

Figure 2:
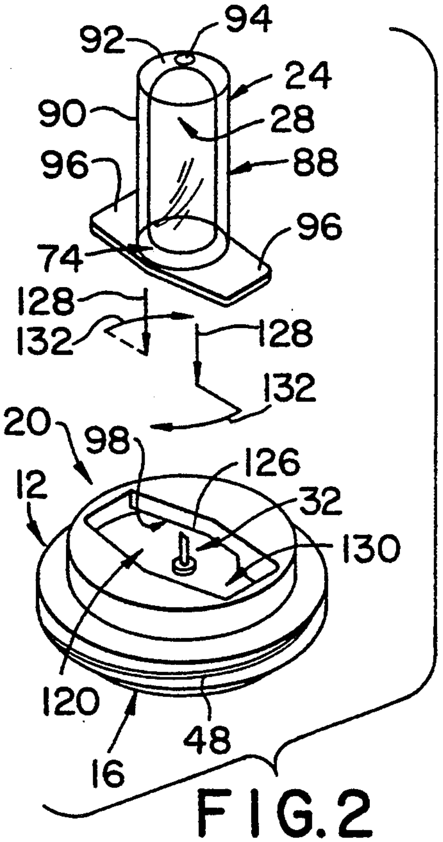
FIG. 2 is a view of the base and the cartridge holder (and the cartridge) of FIG. 1 shown "upside down"

A pair of radially outwardly extending locking flanges 96 are appended to the outer end of the housing 88 as shown in FIG. 1. These locking flanges 96 extend in opposite directions and are arranged to be inserted into a pair of spaced-apart slots 98 formed in the base 12 as shown in FIGS. 2–4. The cartridge holder 24 is also formed to include a cartridge-loading aperture 110 opening into the interior of housing 88 and an annular support shelf 112 for engaging the radially extending annular lip 114 on the underside of closure member 74 to support the sealed cartridge 28 in the interior region 116 of the cartridge holder as shown, for example, in FIG. 3.

Liquid transfer conduit 32 is a tubular member that passes through the base 12 and includes an outlet end 118 opening into the hollow nipple 14 and an inlet end 120 extending in an opposite direction away from the inner side 20 of the base 12 toward the hollow handle 18. The outlet end 118 includes a conical collar 122 and an outlet opening 124 and the inlet end 120 includes an obliquely cut (sharpened) point 126. It is within the scope of the present invention to mold the base 12 to include the liquid transfer conduit 32 or form the base 12 to include an aperture through which the liquid transfer conduit 32 extends.

The sealed cartridge 28 is loaded into the improved pacifier 10 in the following manner. The sealed cartridge 28 is inserted into the interior region 116 of an empty holder 24 to form a subassembly as shown in FIG. 2. This subassembly 24, 28 is moved in direction 128 toward the underside 20 of base 12 so that the sharpened inlet end 120 of the liquid transfer conduit 32 punctures the thin membrane 76 of the closure member 74 and the locking flanges 96 on cartridge holder 24 fit into the main opening 130 on the underside 20 of base 12. These locking flanges 96 can be described as "turn-to-lock" locking flanges because it is only necessary to turn or twist the cartridge holder 24 about its longitudinal axis in directions 132 as shown in FIGS. 2 and 4 to cause each locking flange 96 to move out of the main opening 130 and into one of the adjacent, undercut, side slots 98 formed in the base 12. Insertion of the locking flanges 96 into base slots 98 effectively anchors the cartridge holder 24 to the base 12 and retains the sealed cartridge 28 in place to permit liquid formulation 30 in the sealed cartridge 28 to be withdrawn through the liquid transfer conduit 32. In an alternative embodiment of this invention, sealed liquid formulation containing cartridges for use in this invention can be formed to include the locking flange elements of subassembly 24, 28 so that at least one end of the cartridge is adapted to be breached to provide a port for passage of the contained fluid and so that the side walls proximal to the breachable end are formed to engage in a mechanically locking relationship with complementary locking means on the base so that the cartridge can be positioned and retained in a fluid sealed relationship with the base and/or liquid transfer conduit—thereby eliminating the need for cartridge holder 24.

Assembly of the pacifier 10 is completed by placing the nipple 14 on the outer side 16 of the base 12, placing the hollow handle 18 on the inner side 20 of the base 12, and using the locking ring 22 to engage the external threads on the base 12 and hollow handle 18 to anchor the nipple 14 and hollow handle 18 to the base 12. Vacuum-relief aperture 94 in cartridge holder 24 helps to prevent development of a vacuum in interior region 116 of housing 88 and allow container 72 to collapse during expulsion of liquid formulation 30 into the hollow nipple 14 through the liquid transfer conduit 32.

Figure 6:
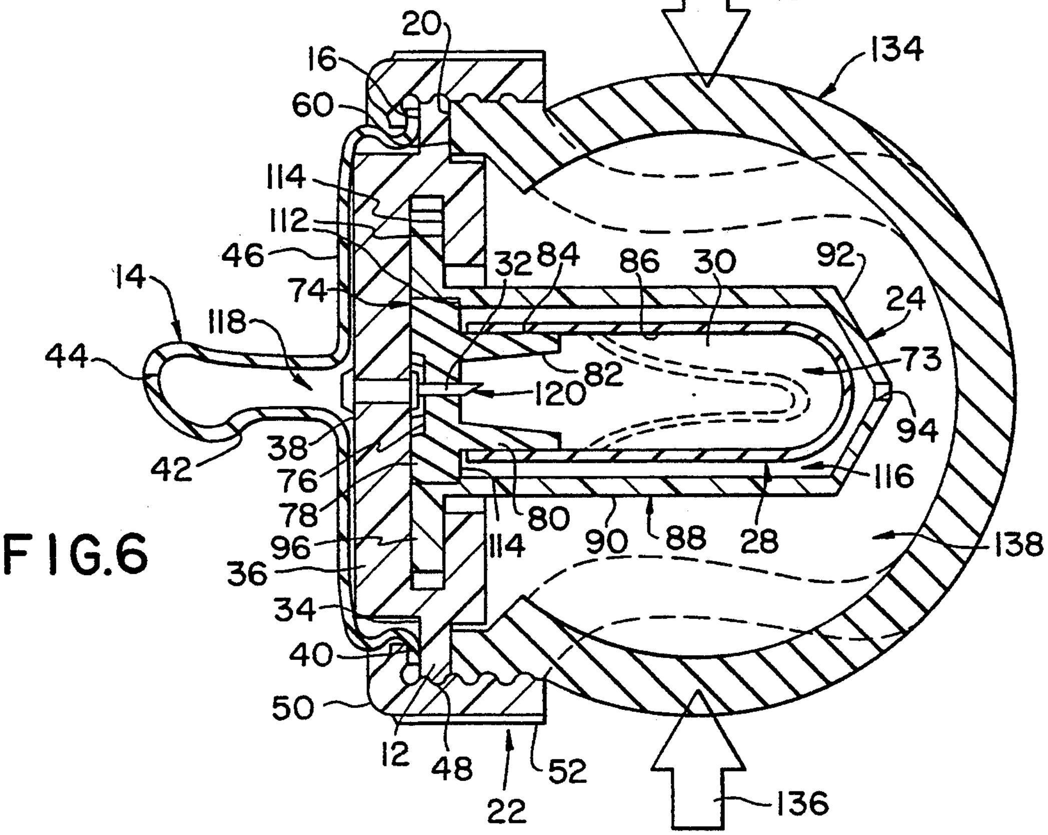
FIG. 6 is a sectional view of an alternative embodiment of the pacifier in accordance with the present invention wherein the hollow handle is a squeeze bulb that can be used to pressurize the interior of the cartridge holder and thereby expel the contained liquid formulation into the nipple for consumption by an infant sucking the nipple.

Another embodiment of a hollow handle is illustrated in FIG. 6. In this embodiment, a deformable hollow squeeze bulb 134 is used in place of the rigid hollow handle 18. As shown diagrammatically, force 136 can be applied by a user to squeeze and deform the squeeze bulb 134 to move the bulb 134 to assume the dotted-line position and pressurize the interior region 138 of the bulb 134. Advantageously, the increased pressure in interior region 138 (and outside of cartridge holder 24) is communicated to the interior region 116 of cartridge holder 24 via the vacuum-relief aperture 94. Such increased pressure is effective to hasten collapse of the collapsible container 72 so that it moves to assume the dotted-line position and expel liquid formulation 30 into the hollow nipple 14 through the liquid transfer conduit 32.

Figure 7:
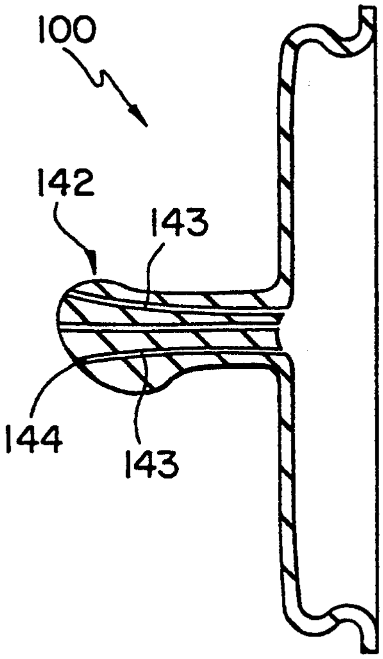
FIGS. 7 and 8 are sectional views of alternate nipple configurations for use in the devices illustrated in FIGS. 1–6.
Figure 8:
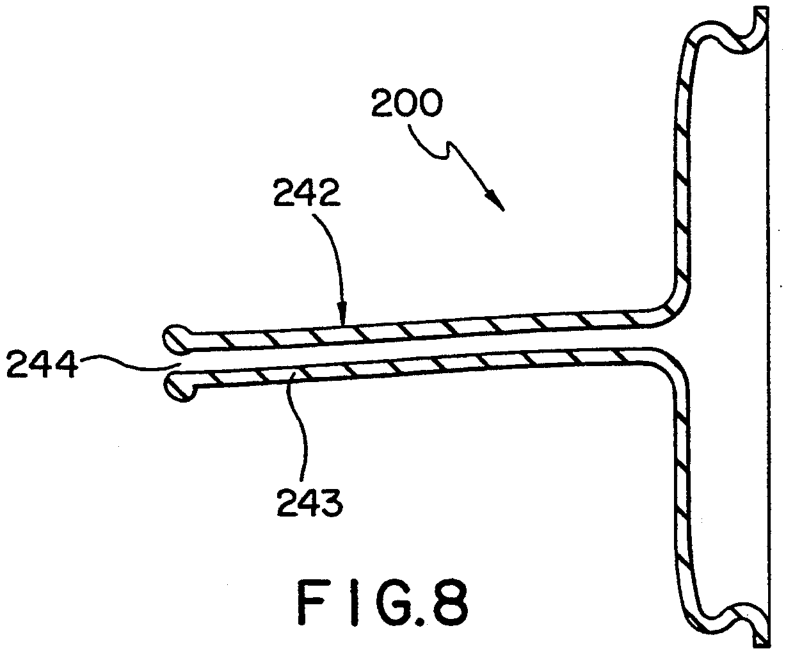

FIGS. 7 and 8 illustrate alternate nipple configurations. In FIG. 7 mouthpiece 142 on nipple 100 is formed to have multiple channels 143 communicating with outlet apertures 144. Multiple channels with multiple ports provide a more natural mechanism for transfer of fluid through the nipple. That configuration further provides minimal internal surface area on the mouthpiece and thereby allows for more efficient transfer of liquid through the mouthpiece. In FIG. 8 mouthpiece 242 on nipple 200 is formed as a small diameter tube 243 communicating with outlet aperture 244. Nipple 200 is preferred for use on present drug delivery devices for use by geriatric patients who may find presentation of more typical nipple construction objectionable. It too can be configured to have multiple small channels communicating with multiple ports.

Although the invention has been described in detail with reference to certain preferred embodiments, variations and modifications exist within the scope and spirit of the invention as described and defined in the following claims.

We claim:

1. A device to facilitate oral administration of a liquid formulation from a sealed cartridge, the device comprising a hollow nipple, a hollow handle formed to include a cavity having a mouth, a base positioned between the nipple and the handle and arranged to cover the mouth of the cavity, means for coupling the nipple to the handle to trap the base therebetween, a cartridge holder positioned in the cavity of the hollow handle for holding the liquid formulation-containing sealed cartridge, and means for communicating liquid formulation between the cartridge and the hollow nipple, the communicating means including means for breaching the liquid formulation-containing sealed cartridge.

2. The device of claim 1, further comprising a liquid formulation-containing sealed cartridge, wherein the sealed cartridge includes a container formed to include a liquid formulation reservoir and an inlet opening and a closure member coupled to the container to close the inlet opening, and wherein the communicating means includes a liquid transfer conduit extending through the base and having a first open end communicating with the hollow nipple and a second open end communicating with the liquid formulation reservoir, the breaching means being positioned at the second open end to breach the closure member during insertion of the liquid transfer conduit into the liquid formulation reservoir of the container.

3. The device of claim 2, wherein the container is a collapsible body made of a flexible material to permit collapse of the container as it is emptied of liquid formulation through the nipple.

4. The device of claim 2, wherein the closure member includes a thin membrane and means for sealingly engaging the container and the membrane to close the inlet opening of the container and position the membrane over the liquid formulation reservoir so that the membrane is punctured or breached during insertion of the second open end of the liquid transfer conduit into the liquid formulation reservoir of the container.

5. The device of claim 1 further comprising a liquid formulation-containing sealed cartridge.

6. The device of claim 5, wherein the cartridge holder includes means for mechanically locking the sealed cartridge to the base in conjunction with insertion of the communicating means into the sealed cartridge.

7. The device of claim 6, wherein the sealed cartridge includes a container formed to include a liquid formulation reservoir and an inlet opening and a closure member coupled to the container to close the inlet opening and the locking means is coupled to the closure member.

8. The device of claim 6, wherein the cartridge holder includes a housing formed to include a cartridge-receiving chamber, means for supporting the sealed cartridge in the cartridge-receiving chamber, the locking means includes a locking flange appended to the housing, and the base is formed to include slot means for receiving the locking flange of the cartridge holder in response to rotation of the cartridge holder about a longitudinal axis thereof to anchor the locking flange to the base and support the sealed cartridge adjacent to the base in the cavity of the hollow handle.

9. The device of claim 6, wherein the cartridge holder includes a housing formed to include a cartridge-receiving chamber, means for supporting the sealed cartridge in the cartridge-receiving chamber, and a locking flange appended to the housing and the base includes means for releasably anchoring the locking flange to the base conjunction with insertion of the communicating means into the sealed cartridge.

10. The device of claim 9 wherein the base is formed to include a locking flange-receiving slot to define the anchoring means.

11. The device of claim 1, wherein the base includes means for releasably anchoring the cartridge holder to the base in conjunction with the insertion of the communicating means into the sealed cartridge.

12. The device of claim 1, wherein the hollow nipple includes a liquid-dispensing mouthpiece including a liquid-receiving end and a diaphragm appended to the mouthpiece at the liquid-receiving end, and the coupling means includes a locking ring coupled to the diaphragm and the hollow handle.

13. The device of claim 12, wherein the base includes external threads, the hollow handle includes external threads, and the locking ring includes means for threadedly engaging the external threads on the base and the hollow handle to trap the base in a fixed position between the hollow nipple and the hollow handle.

14. A device for oral administration of liquid formulations, the device comprising a base having an outer side and an inner side, a liquid transfer conduit passing through the base and having a first open end on the outer side of the base and a second open end on the inner side of the base, a hollow nipple mounted on the outer side of the base to receive liquid formulations discharged through the first open end of the liquid transfer conduit, a hollow handle formed to include a cavity having a mouth, the hollow handle being mounted on the inner side of the base to present the open mouth toward the base and receive the second open end of the liquid transfer conduit in the cavity, a liquid formulation-containing cartridge situated in the cavity of the hollow handle, and means for supporting the cartridge in a fixed position in the cavity of the hollow handle, the supporting means including a housing formed to include a cartridge-receiving chamber and a locking flange appended to the housing and sized for engagement with the inner side of the base, the liquid transfer conduit including means for puncturing the liquid formulation-containing cartridge to place the second open end of the liquid transfer conduit and the liquid formulation-containing cartridge in fluid communication during positioning and locking of the cartridge to the base using the locking flange.

15. The device of claim 14, wherein the means includes an annular seat surrounding the cartridge-receiving chamber and facing toward the inner side of the base and the cartridge includes a lip engaging the annular seat.

16. The device of claim 14, wherein the base is formed to include a locking flange-receiving slot having an opening formed in the inner side of the base and located in the cavity formed in the hollow handle.

17. The device of claim 14, wherein the base is formed to include slot means for receiving the locking flange of the supporting means in response to rotation of the supporting means about a longitudinal axis thereof to anchor the locking flange to the base in the cavity of the hollow handle.

18. The device of claim 14, wherein the cartridge includes a collapsible container situated in the cartridge-receiving chamber of the housing and formed to include a liquid formulation reservoir communicating with the second open end of the liquid transfer conduit, the housing is formed to include aperture means for communicating pressure developed in the cavity formed in the hollow handle into the cartridge-receiving chamber to encounter the collapsible container, and the hollow handle is made of a manually squeezable and deformable material to provide means for manually pressurizing the cavity formed in the hollow handle and in the cartridge-receiving chamber using the aperture means to apply pressure to the collapsible container to hasten the collapse of the collapsible container ant urge liquid formulation out of the liquid formulation reservoir, through the liquid transfer conduit, and into the hollow nipple for oral consumption.

19. The device of claim 14, wherein cartridge includes a collapsible container situated in the cartridge-receiving chamber of the housing and formed to include a liquid formulation reservoir communicating with the second open end of the liquid transfer conduit, the housing is formed to include aperture means for communicating pressure developed in the cavity formed in the hollow handle into the cartridge-receiving chamber to encounter the collapsible container and the hollow handle is made of a manually squeezable and deformable material to provide means for manually pressurizing the cavity formed in the hollow handle and in the cartridge-receiving chamber using the aperture means to apply pressure to the collapsible container to hasten the collapse of the collapsible container and urge liquid formulation out of the liquid formulation reservoir, through the liquid transfer conduit, and into the hollow nipple for oral consumption.

20. A device to facilitate oral administration of liquid formulations the device comprising a hollow nipple having a perforate liquid-dispensing end, a base having proximal and distal sides relative to said nipple, said base sized to prevent swallowing of said nipple, said distal side of the base formed to have a port in fluid communication with the hollow nipples, means for supporting a liquid formulation-containing cartridge in liquid-sealed alignment with said port, means for breaching said sealed cartridge simultaneously as it is locked in liquid sealed alignment with the port using the supporting means, and a hollow handle formed to include a cavity having a mouth, the hollow handle being mounted on the distal side of the base to present the mouth toward the base and receive the liquid formulation-containing sealed cartridge in the cavity, the supporting means a cartridge holder having a housing formed to include a cartridge-receiving chamber and means for positioning the sealed cartridge in the cartridge-receiving chamber, the sealed cartridge including a collapsible container situated in the cartridge-receiving chamber of the housing and being formed to include a liquid formulation reservoir communicating with the port, the housing being formed to include aperture means for communicating pressure developed in the cavity formed in the hollow handle into the cartridge-receiving chamber to encounter the collapsible container, the hollow handle being made of a manually deformable material to provide means for manually pressurizing the cavity formed in the hollow handle and in the cartridge-receiving chamber through the aperture means to apply pressure to the collapsible container to hasten the collapse of the collapsible container and urge liquid formulation out of the liquid formulation reservoir, through the port, and into the hollow nipple for oral consumption.

* * * * *